United States Patent
Kasai et al.

(10) Patent No.: US 9,566,236 B2
(45) Date of Patent: Feb. 14, 2017

(54) PROTEOLIPOSOME, PRODUCTION METHOD THEREOF, AND BIOCHIP

(75) Inventors: Nahoko Kasai, Atsugi (JP); Chandra Sekar Ramanujan, Oxford (GB); Keiichi Torimitsu, Atsugi (JP); John F. Ryan, Oxford (GB)

(73) Assignees: Nippon Telegraph And Telephone Corporation, Tokyo (JP); Isis Innovation Ltd., Oxford (GB)

( * ) Notice: Subject to any disclaimer, the term of this patent is extended or adjusted under 35 U.S.C. 154(b) by 1556 days.

(21) Appl. No.: 12/324,302

(22) Filed: Nov. 26, 2008

(65) Prior Publication Data

US 2010/0129433 A1     May 27, 2010

(51) Int. Cl.
*A61K 9/127* (2006.01)

(52) U.S. Cl.
CPC .................................. *A61K 9/127* (2013.01)

(58) Field of Classification Search
None
See application file for complete search history.

(56) References Cited

U.S. PATENT DOCUMENTS

2005/0153357 A1*   7/2005   Eichler et al. ............... 435/6

OTHER PUBLICATIONS

Mimms et al (1981 Biochemistry 20:833-840).*

Lichtenberg, Dov, et al., "Phase boundaries in mixtures of membrane-forming amphiphiles and micelle-forming amphiphiles," Biochimica et Biophysica Acta, 1508, pp. 1-19 (2000), Elsevier Science B.V.

Brockmann, Rainer A., et al., "Spontaneous Formation of Detergent Micelles around the Outer Membrane Protein OmpX," Biophysical Journal, vol. 88, pp. 3191-3204 (May 2005), Biophysical Society.

Cottingham, Ian R., et al., "The reconstitution of L-3-glycerophosphate-cytochrome c oxidoreductase from L-3-glycerophosphate dehydrogenase, ubiquinone-10 and ubiquinol—cytochrome c oxidoreductase," Biochemistry Journal, 192, pp. 19-31 (1980), The Biochemical Society.

Vaithianathan, Thirumalini, et al., "Neural Cell Adhesion Molecule-associated Polysialic Acid Potentiates a-Amino-3-hydroxy-5-methylisoxazole-4-propionic Acid Receptor Currents," The Journal of Biological Chemistry, vol. 279, No. 46, pp. 47975-47984 (Nov. 12, 2004), The American Society for Biochemistry and Molecular Biology, Inc.

* cited by examiner

*Primary Examiner* — Christopher M Gross
(74) *Attorney, Agent, or Firm* — Harness, Dickey & Pierce, P.L.C.

(57) ABSTRACT

A proteoliposome, which is obtained by removing a surfactant from a mixed solution including lipid, membrane proteins and the surfactant, wherein the content of the surfactant in the mixed solution is equal to or more than 1.5 times of the sum of a maximum amount of the surfactant associating with the lipid and a maximum amount of the surfactant associating with the membrane protein. A biochip wherein the above-described proteoliposome is spread on a substrate. A method for producing a proteoliposome by removing a surfactant from a mixed solution including lipid, membrane proteins and the surfactant, wherein the content of the surfactant in the mixed solution is made equal to or more than the sum of a maximum amount of the surfactant associating with the lipid and a maximum amount of the surfactant associating with the membrane protein.

5 Claims, 2 Drawing Sheets

PROTEOLIPOSOME, PRODUCTION METHOD THEREOF, AND BIOCHIP

BACKGROUND OF THE INVENTION

Field of the Invention

The present invention relates to a proteoliposome, a production method thereof, and a biochip.

Description of the Related Art

The post-genome era has come, and research and development in which proteins purified from a living body are used for various purposes have been actively carried out. Among them, membrane proteins have attracted attention as a new target of drug discovery.

A receptor protein which is a membrane protein exists in a biological membrane, plays an important role in intravital signal transduction, and its impairment of function is largely concerned with diseases. In recent years, approximately 50% of existing drugs and approximately 70% of drugs under research and development are said to target the membrane protein.

In addition, research in a new field called nanomedicine wherein molecules are used in a nanometer range under controlled activity for drug discovery, as typified by a drug delivery system (DDS), has appeared as well, and there is a case where it is actually used for a medical treatment in the United States.

More specifically, a nanometer-sized liposome is formed from a lipid bilayer membrane (hereinafter, may be simply referred to as a "lipid membrane"), a receptor protein is embedded in the surface of the liposome, and a drug is encapsulated therein. Consequently, a localized delivery by a molecule identification ability of the receptor protein can be realized. The drug in the proteoliposome (liposome in which membrane proteins are embedded) can be selectively administered to a target cell. This technique is expected to be applied not only to a treatment for lungs, eyes or skin, but also to a treatment for cancer, neurodegenerative diseases, or cardiovascular diseases.

For a quick diagnosis or in drug discovery, a biochip is used in which proteins or antibodies are immobilized on a substrate to observe the response by various methods such as a surface plasmon resonance method (SPR method). However, since detection/observation of conformational change in the protein is performed by holding proteins having activity with a number of molecules on a substrate, followed by detecting an average conformational change in proteins therein, it has been difficult to precisely examine the connection between the structure/conformational change of a single protein molecule and its function.

Furthermore, exploring the connection between the structure/conformational change and the function has been carried out by observing the structure and conformational change of a single protein molecule. For example, Nakagawa et al. have observed the structural differences of membrane proteins before and after stimulation by using an electron microscope. However, this method is an observation method carried out by scattering of a number of proteins on a substrate, and thus it is difficult to determine the orientation of the protein under observation. Therefore, it has been necessary to observe dozens of or tens of thousands of protein molecules and carry out image processing in order to know the orientation of the protein by analogy and determine the structure of the protein molecule. In addition, since proteins are frozen according to the method, it has not been possible to make an observation of proteins retaining their activity.

An atomic force microscope (AFM) is capable of observing a nanometer-sized object in a solution, and accordingly a protein retaining activity can be observed, one molecule at a time. Consequently, if a condition wherein membrane proteins are reconstituted in a lipid membrane is created so as to mimic that in vivo, it is believed that detailed knowledge related to the function of membrane proteins in an organism can be obtained by a single-molecule observation by AFM.

When a part of protein is immobilized on a substrate or a protein interacts with a substrate, it is thought that the protein does not change in the same manner as in vivo. In particular, since membrane proteins exhibit a function only in a state of being in a biological membrane, it is necessary to observe membrane proteins that being constituted in a lipid bilayer membrane mimicking an organism, so as to examine closely the connection between the structure and function.

As mentioned above, it is very important to reconstitute membrane proteins in a lipid membrane, particularly in the pharmacological or industrial application of membrane proteins.

Reconstitution of membrane proteins to a lipid membrane is carried out mainly for purposes such as (1) DDS using proteoliposomes, (2) two-dimensional crystallization of membrane proteins for X-ray structure analysis and (3) channel activity measurement by an electrophysiological method.

In (1), as many membrane proteins as possible are embedded in a liposome because it is believed that the greater the number of membrane proteins, the better the drug effect. However, even if a large number of membrane proteins are embedded in a liposome, they aggregate in a proteoliposome, and as a result, the number of membrane proteins which can fulfill the function effectively was considered to be small.

Also in (2), a large number of membrane proteins are embedded in a lipid membrane in a state where the proteins are aligned while being in contact with each other, so as to give a crystalline structure. Also in (3), the aggregation has not been a matter as long as there are membrane proteins having activity. That is, examination on reconstituting membrane proteins by dispersing at a predetermined interval without causing aggregation has not been practically carried out. Therefore, a biochip which is suitable for use in observation of a single membrane-protein molecule or the like has been demanded.

For a structural observation at the single molecular level, membrane proteins need to be oriented in the same orientation for reconstitution, in addition to their needing to be distanced at a predetermined interval without each being aggregated with the others. In addition, upon the spreading on a substrate, membrane proteins need to be placed at the center of a lipid domain (region including a lipid membrane) in order to perform an accurate structural observation by making the effect from surrounding lipid molecules uniform.

For all of those reasons, it is desirable to control the aggregation of membrane proteins to be constituted in a proteoliposome, and to spread membrane proteins at a predetermined interval on a substrate of a biochip by controlling the aggregation. Moreover, it is desirable to control the aggregation to reconstitute membrane proteins, from the viewpoint of reducing the amount of membrane proteins to be used since they are generically difficult to obtain or a valuable resource.

SUMMARY OF THE INVENTION

An object of the invention is to provide a proteoliposome in which the aggregation of membrane proteins to be reconstituted in a lipid membrane is controlled, and a method for producing the proteoliposome.

Another object of the invention is to provide a biochip which is used to observe a single membrane-protein molecule, wherein the aggregation of membrane proteins is controlled and the membrane proteins are dispersed and spread at a predetermined interval on a substrate.

The proteoliposome according to an aspect of the invention is obtained by removing a surfactant from a mixed solution including lipid, membrane proteins and the surfactant, wherein the content of the surfactant in the mixed solution is equal to or more than the 1.5 times of sum of a maximum amount of the surfactant associating with the lipid and a maximum amount of the surfactant associating with the membrane protein.

In the biochip according to an aspect of the invention, the proteoliposome is spread on a substrate.

In the biochip according to an aspect of the invention, the substrate preferably includes at least one kind selected from the group consisting of mica, $SiO_2$, SiN, Au and Pt.

A method for producing a proteoliposome according to an aspect of the invention includes removing a surfactant from a mixed solution obtained by mixing lipid, membrane proteins and the surfactant, the method being characterized in that the content of the surfactant in the mixed solution is equal to or more than the sum of a maximum amount of the surfactant associating with the lipid and a maximum amount of the surfactant associating with the membrane protein.

In the proteoliposome according to an aspect of the invention, aggregation of membrane proteins reconstituted in a lipid membrane is controlled. According to the method of an aspect of the invention for producing a proteoliposome, a proteoliposome wherein the aggregation of membrane proteins reconstituted in a lipid membrane is controlled can be obtained.

A biochip according to an aspect of the invention is one in which aggregation of membrane proteins is controlled and the membrane proteins are dispersed and spread at a predetermined interval on a substrate. Therefore, the biochip is suitably used for observation of the membrane protein at a single molecular level, or the like.

DETAILED DESCRIPTION OF THE INVENTION

Proteoliposome and Production Method Thereof

Figure 1:
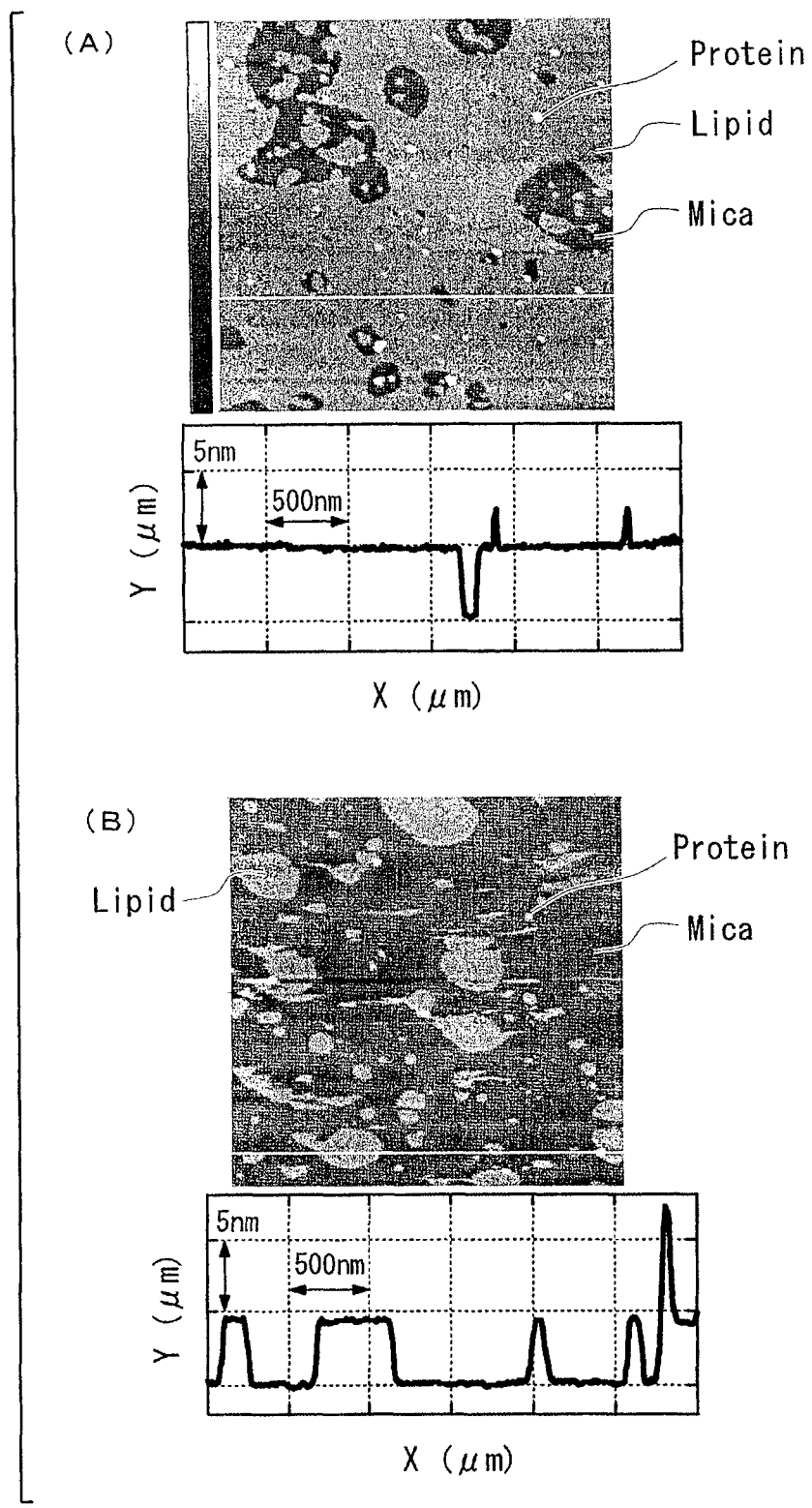
FIG. 1 shows an AFM image of Example 1 and Comparative Example 1.

A proteoliposome according to an embodiment of the invention is a liposome including membrane proteins which is obtained by removing a surfactant from a mixed solution prepared by mixing lipid, membrane proteins and the surfactant. Examples of the medium of the mixed solution may include aqueous media such as water, saline and a buffer solution. Examples of the buffer solution may include lactic acid, phosphoric acid, citric acid, boric acid, trishydroxymethylaminomethane, 2-(4-(2-hydroxyethyl)-1-piperazinyl) ethane sulfonic acid (HEPES) and the like.

The lipid to be used may be any of those generally used for the production of liposome, and examples thereof may include egg phosphatidylcholine, egg phosphatidylglycerol, hydrogenated soy phosphatidylcholine (HSPC), distearoylphosphatidylcholine, distearoylphosphatidylglycerol, phosphatidylcholine (PC), phosphatidylglycerol (PG), lecithin, beta, glycolipid, γ-dipalmitoyl-α-lecithin, sphingomyelin (SPM), phosphatidylserine (PS), phosphatidic acid, N-(2,3-di(9-(Z)-octadecenyloxy))-prop-1-yl-N,N,N-trimethylammonium chloride, phosphatidylethanolamine (PE), lysolecithin, lysophosphatidylethanolamine, phosphatidylinositol (PI), cephalin, cardiolipin, cerebroside, dicetyl phosphate, dioleoyl phosphatidylcholine, dipalmitoyl phosphatidylcholine, dipalmitoyl phosphatidylglycerol, dioleoyl phosphatidylglycerol, palmitoyl-oleoyl-phosphatidylcholine, distearoylphosphatidylcholine (DSPC), dimyristoylphosphatidylcholine (DMPC), dimyristoylphosphatidylglycerol, (DMPG), stearoyl-palmitoyl-phosphatidylcholine, di-palmitoyl-phosphatidylethanolamine, di-stearoyl-phosphatidylethanolamine, di-myristoyl-phosphatidylserine (DMPS), di-oleoyl-phosphatidylcholine, di-oleoyl-palmitoyl-phosphatidylcholine, monosialoganglioside and the like.

These lipids may be used singly or in combination of two or more kinds thereof.

The membrane protein may be any of those disposed in a lipid bilayer of a cell membrane in vivo, and examples thereof may include ionotropic receptors, G protein-coupled receptors and the like.

Examples of the ionotropic receptor may include TRP (Transient Receptor Potential) channels (Subunits are TRPV1, TRPV2, TRPV3, TRPV4, TRPV5, TRPV6, TRPV8, TRPA1, TRPC1, TRPC2, TRPC3, TRPC4, TRPC5, TRPC6, TRPC7, TRPM1, TRPM2, TRPM3, TRPM4, TRPM5, TRPM6, TRPM7, TRPM8, TRPN1, TRPML1, TRPML2, TRPML3, TRPY1, TRPP1, TRPP2, TRPP3, TRPP4 and TRPP5) involved in cellular signal transduction, temperature sensitivity, inflammation and pain; ATP receptors (Subunits are P2X1, P2X2, P2X3, P2X4, P2X5, P2X6 and P2X7) involved in cellular signal transduction and pain; serotonin receptors (Subunits are 5-HT1, 5-HT2, 5-HT4, 5-HT6 and 5-HT7) involved in cellular signal transduction and affectivity; NMDA receptors (Subunits are NR1, NR2A and NR2B) involved in cellular signal transduction and excitatory neurotransmission; AMPA receptors (Subunits are GluR1, GluR2, GluR3 and GluR4) involved in cellular signal transduction and excitatory neurotransmission; kainate receptors (Subunits are GluR5 and GluR7) involved in cellular signal transduction and excitatory neurotransmission; GABA receptors (Subunits are GABAA and GABAC) involved in cellular signal transduction and inhibitory neurotransmission; and the like.

Examples of the G protein-coupled receptor may include adenosine receptors (A1, A2A, A2B and A3) involved in cellular signal transduction; ATP receptors (P2Y1, P2Y2, P2Y4, P2Y6, P2Y11, P2Y12, P2Y13 and P2Y14) involved in cellular signal transduction; serotonin receptors (5-HT3) involved in cellular signal transduction; adrenergic receptors (α1, α2, β1 and β2) involved in cellular signal transduction and pain; metabotropic glutamate receptors (mGluR1, mGluR2, mGluR3, mGluR5, mGluR6, mGluR7 and mGluR8) involved in cellular signal transduction; GABA receptors involved in cellular signal transduction; opioid receptors (ν receptor, δ receptor and κ receptor) involved in cellular signal transduction and pain; and the like.

These membrane proteins may be used singly or in combination of two or more kinds thereof.

The membrane protein may be bonded to a fluorescent material by a genetic engineering technique. A proteoliposome having a specific membrane protein can be easily identified by binding to a fluorescent material.

As the fluorescent material, known materials usually used for binding with proteins can be used, and examples thereof may include fluorescent proteins such as GFP, CFP and YFP. By allowing a fluorescent material to bond to a position outside the lipid bilayer membrane of a membrane protein in a proteoliposome, as well as allowing a fluorescent material to bond to a substance binding to the membrane protein, a conformational change of the membrane protein at a single molecular level due to such binding can be detected according to FRET (Fluorescence Resonance Energy Transfer).

Nonionic surfactants, anionic surfactants, cationic surfactants or zwitterionic surfactants can be used as a surfactant.

The nonionic surfactant may include D-octyl-n-glucoside, polyoxyethylene alkyl ether (AE), polyoxyethylene alkylphenol ether, alkyl glucoside (AG), polyoxyethylene fatty acid ester, sucrose fatty acid ester, sorbitan fatty acid ester, polyoxyethylene sorbitan fatty acid ester, fatty acid alkanolamide, diethanolamide, Tween, Triton and the like.

Examples of the anionic surfactant may include cholate, deoxycholate, glycolate, fatty acid sodium salt, monoalkyl sulfate, alkyl polyoxyethylene sulfate, alkyl benzene sulfonate, monoalkyl phosphate and the like.

Examples of the cationic surfactant may include alkyl trimethylammonium salt, dialkyl dimethylammonium salt, alkyl benzyl dimethyl ammonium salt, cetyltrimethylammonium bromide (CTAB) and the like.

Examples of the zwitterionic surfactant may include 3-(dodecyldimethyl-ammonio)propanesulfonate, polyoxyethylene alkyl ether, sorbitan fatty acid ester, fatty acid diethanolamide alkylmonoglyceryl ether, 3-((3-cholamidopropyl)dimethylammonio)-1-propanesulfonate (CHAPS), myristyl sulfobetaine (SB3-14) and the like.

These surfactants may be used singly or in combination of two or more kinds thereof.

The proteoliposome of the invention may be filled with components such as drugs in the lipid membrane or the inner cavity, if needed. Examples of these components may include anticancer drug, neurologic drug, cardiovascular drug and the like.

Moreover, a labeling reagent such as a fluorescent reagent may be filled into the inner cavity. By filling a different labeling reagent into each proteoliposome having a different membrane protein, they can be easily identified. Examples of the labeling reagent may include FITC (registered trademark, fluorescein), rhodamine, Cy3 (registered trademark), Cy5 (registered trademark) and the like.

An average particle diameter of the proteoliposome is preferably 50 nm to 5 μm. When the average particle diameter is 50 nm or more, it is easy to reconstitute membrane proteins at a predetermined interval in a lipid membrane. In addition, when using DDS or the like, the amount of drugs or the like to be filled in the inner cavity can be increased.

The average particle diameter of the proteoliposome is an average value of values obtained from proteoliposome particle diameters distribution obtained by an observation of a predetermined number of proteoliposomes with a dynamic light scattering method.

Furthermore, intervals of the membrane protein are preferably 50 to 100 nm in the proteoliposome. When the intervals of membrane proteins are 50 nm or more, aggregation of the membrane proteins can be easily suppressed. When the intervals of membrane proteins are 100 nm or less, a proteoliposome having an adequate amount of membrane proteins can be obtained with ease.

Hereinafter, a method for producing a proteoliposome of the invention will be illustrated.

The proteoliposome of the invention can be obtained by removing a surfactant from a mixed solution obtained by mixing lipid, membrane proteins and the surfactant.

A content of lipid in the mixed solution is preferably 1.0 to 5.0 mM based on the total amount of the mixed solution, more preferably 2.0 to 3.0 mM.

A content of the membrane protein in the mixed solution differs depending on the kind of membrane protein, but it is preferably $1.0 \times 10^{-5}$ to $1 \times 10^{-4}$ mol per 1 mol of lipid, more preferably $3.3 \times 10^{-5}$ to $7.5 \times 10^{-5}$ mol. In the case where the content of the membrane protein is $1.0 \times 10^{-5}$ or more per 1 mol of lipid, sufficient amount of the membrane protein can be easily embedded in a proteoliposome. When the content of the membrane protein is $1 \times 10^{-4}$ mol or less per 1 mol of lipid, the membrane proteins can be reconstituted at a predetermined interval in a lipid membrane without aggregating membrane proteins.

A content of the surfactant in the mixed solution which is used for producing a proteoliposome is 1.5 times of the total amount $(W_A+W_B)$ of the maximum amount of the surfactant associating with the lipid $W_A$ and the maximum amount of the surfactant associating with the membrane protein $W_B$ or more, preferably 2.0 times or more. In the case where the content of the surfactant is 1.5 times of the total amount $(W_A+W_B)$ or more, a sufficient amount of the surfactant associates with lipid and membrane proteins to be stable in the mixed solution, and as a result, aggregation of membrane proteins can be suppressed in the mixed solution. In addition, since membrane proteins gradually move into the lipid membrane to be reconstituted, aggregation of membrane proteins can be suppressed in the obtained proteoliposome. Accordingly, a proteoliposome in which the membrane proteins leave a predetermined space between each other to reconstitute a lipid membrane can be obtained with aggregation of the membrane proteins suppressed. The upper limit of the surfactant content may be an amount soluble in an aqueous solvent since adverse effects are small even if there is an excess of surfactant.

The maximum amounts $W_A$ of the foregoing surfactant can be found as described below is 3 mol per 1 mol of lipid molecules in case of octyl glucoside according to Lichtenberg, et al., Biochimica et Biophysica Acta, 1508, 1-19 (2000). An association number of the surfactant to transmembrane domain portions of membrane proteins, that is $W_B$, is considered in Bockman R. A. et al., Biophysical Journal, 61, 1176-1183 (2005). That is, when the length of a transmembrane portion is 2.5 nm and the diameter is 2.8 nm, the association number of the surfactant DHPC is 80 molecules. The association number ($W_B$) is estimated from the kinds of the surfactant or the size of the transmembrane portion.

For example, in the case where the lipid is mixed lipid (mass average molecular weight 800) of PC (egg yolk) and PS (derived from swine brain) which are mixed in the proportion of 3:1 and the surfactant is octyl glycoside (OG, molecular weight 292), the surfactant associating with 1 mol of the mixed lipid is 3 mol. In the case where the membrane protein is an AMPA receptor and the surfactant is OG, the surfactant associating with 1 mol of the AMPA receptor is 240 mol. Accordingly, in the case where the foregoing mixed lipid m mol and a membrane protein n mol are used, the amount of the surfactant is $(W_A+W_B)=(3m+240n)$ or more.

The mixed solution can be prepared by adding lipid, membrane proteins and a surfactant to an aqueous medium to dissolve by stirring. Moreover, when encapsulating a drug or the like in a proteoliposome, those components may be added in the mixed solution.

A temperature when mixing the lipid, membrane proteins and surfactant is preferably the phase transition temperature of the lipid or higher, and preferably 37° C. or less in order to maintain activities of membrane proteins.

The surfactant can be removed from the mixed solution by a known method, and examples thereof may include dialysis using a cellulosic semipermeable membrane or the like and a bead method using a hydrophobic adsorbent (beads).

The dialysis is preferably carried out at about 4° C. from over a few days to a week.

By removing the surfactant in the mixed solution gradually by these methods, a liposome which is composed of a lipid bilayer membrane is formed from stabilized lipid in the mixed solution while stabilized membrane proteins in the mixed solution gradually move into the lipid bilayer membrane, and then are reconstituted in a liposome to be stabilized.

The particle diameter of the proteoliposome can be made uniform by an ultrasonic agitation method. A sonicator to be used may be either type of a probe or bath. However, the probe type has a possibility that metal ions are mixed in the mixed solution since a metal tip comes into contact with the mixed solution. In addition, it is difficult to obtain a proteoliposome having excellent uniformity since the ultrasonic waves are unequal in the mixed solution. Therefore, the sonicator is preferably a bath type.

The proteoliposome of the invention can suppress aggregation of membrane protein reconstituting in the lipid membrane and control the state to be dispersed at a predetermined interval by controlling the amount of the surfactant to the total amount of lipid and membrane proteins. Furthermore, the amount of the membrane proteins in a proteoliposome can be easily controlled by changing the ratio of lipid and membrane protein.

The proteoliposome of the invention can be used in a state of a proteoliposome for observation through an electron microscope or the like in order to examine the relationship between the structure and conformational change and its function of a membrane protein. The proteoliposome can be used in the field of nanomedicine such as DDS by filling drugs or the like in the inner cavity.

Biochip

A biochip of the invention is one in which the above-mentioned proteoliposome of the invention is spread on a substrate.

A substrate of the invention may be used for a substrate of a biochip, and it is preferably a substrate including one or more kinds selected from the group consisting of glass, mica, $SiOH/SiN/SiO_2$, Au and Pt.

A microstructure may be formed on the surface of the substrate in order to allow an easy spread of a lipid bilayer membrane.

Examples of the method of spreading the proteoliposome on a substrate may include a vesicle fusion method. The vesicle fusion method is a method of transferring a lipid bilayer membrane onto the substrate by the interaction between the lipid bilayer membrane of a vesicle and the substrate, by immersing the substrate in a solution containing a spherical endoplasmic reticulum called a vesicle (a proteoliposome of the invention). It may be a method of adding dropwise the foregoing solution onto the substrate.

In the case where the proteoliposome is spread on a substrate by this method, the substrate can be modified in order to improve the interaction between the surface of the substrate and the lipid bilayer membrane. Examples of the modification method may include a method in which the surface of the substrate is modified with an amino group-containing substance to change to hydrophilicity, and the interaction between the substrate and the lipid bilayer membrane is improved by an electrostatic force.

Furthermore, a lipid bilayer membrane is formed on a substrate in advance, and the proteoliposome is spread on the lipid bilayer membrane. This leads to fusion of the lipid bilayer membrane on the substrate with the lipid bilayer membrane of the proteoliposome, and then membrane proteins in the proteoliposome are reconstituted to a lipid bilayer membrane on the substrate. Examples of the method of forming a lipid bilayer membrane on a substrate in advance may include a method in which the above-mentioned vesicle fusion method is carried out using a liposome not containing membrane proteins.

For the observation method of the membrane protein in a biochip, for example, AFM, scanning probe microscopy (SPM) other than AFM, total internal reflection fluorescence (TIFR), optical microscopy or the like can be used. Among them, AFM is preferably used for the observation of a single membrane-protein molecule.

Reconstituted membrane proteins in the lipid bilayer membrane are closer to the intravital state than membrane proteins remaining purified. For that reason, more reliable results can be obtained in a drug screening or biological use by using membrane proteins with the membrane proteins reconstituted in the lipid bilayer membrane like this.

Moreover, when a lipid domain (region composed of a lipid bilayer membrane on a substrate) is small, it is easy to move the membrane protein to the end of the lipid domain since it is energetically stable. As described above, when membrane proteins are at the end of the lipid domain, it is difficult to observe the membrane protein accurately since the influence from the surrounding lipid molecules becomes uneven, and interaction with the substrate may occur.

As for the biochip of the invention, a lipid domain having a sufficient size is formed on a substrate using the foregoing proteoliposome, and further, the membrane protein is dispersed at a predetermined interval in the lipid domain to be reconstituted with aggregation of the membrane protein suppressed. As a result, sufficient membrane proteins which are suitable for observation of the center of the lipid membrane can be obtained.

The size of the lipid domain is preferably 1 $\mu m^2$ or more. The size of the lipid domain can be adjusted by adjusting the composition of the mixed solution and the dialysis conditions such as increasing the amount of the lipid to be used for producing a proteoliposome, followed by regulating the surfactant accordingly.

The interval of the membrane proteins in the lipid bilayer membrane of a biochip is preferably 50 to 100 nm. When the interval between the membrane proteins is 50 nm or more, it is easy to observe and analyze the single membrane-protein molecule. When the interval between the membrane proteins is 100 nm or less, a membrane protein locating at the center of the lipid domain can be easily obtained and it becomes easy to observe the membrane protein in the same state as in vivo.

The membrane protein in the biochip of the invention is reconstituted to face the same orientation. Specifically, it is energetically more stable for a transmembrane domain of the membrane protein to exist inside the lipid domain because of a hydrophobic interaction with an alkyl chain of a lipid molecule in the lipid membrane. Therefore, the membrane protein is reconstituted by locating the transmembrane domain inside the lipid membrane and the rest on the lipid membrane to face the same orientation. Consequently, the structure and conformational change of the membrane protein can be examined by observing a single molecule without observing a number of membrane proteins and knowing the orientation by analogy.

In addition, since the structure of the membrane protein is maintained by reconstitution, its function is also maintained. Therefore, a response of the membrane protein to a drug can be directly examined effectively and efficiently by observing the membrane protein maintaining the activity at a single molecular level. According to this, a performance of a drug target with respect to a specific membrane protein receptor dramatically improves. Consequently, it is expected to be widely used not only in drug screening in drug discovery but also in the field of diagnosis in which membrane proteins are detected.

In the conventional method for producing a proteoliposome, a small amount of a surfactant is used for reconstitution, and membrane proteins could not be dispersed with sufficient intervals for a lipid membrane while suppressing the aggregation. For example, in the method described in BioChem. J., 192, 19 (1980), the proportion of membrane protein to the surfactant was approximately 1000:1 in a mixed solution of lipid, membrane proteins and a surfactant, this amount of surfactant being very small, and the membrane proteins were aggregated.

In contrast with this, aggregation of membrane proteins can be suppressed in the proteoliposome and biochip of the invention described above. In addition, a membrane protein which maintains activity can be observed at a single molecular level under the same conditions as in vivo because those membrane proteins can be dispersed with intervals in a lipid bilayer membrane for reconstitution. Obtaining such a substrate is an important technique in which conformational change of the membrane protein can be observed at a single molecular level in real time, and this technique can be applied to realization of a very sensitive and extremely fine biosensor chip, or the like. Accordingly, it is extremely effective in the field of a combination of nanotechnology and biotechnology whose development is considered to be significant in the future.

Furthermore, with regard to the proteoliposome according to the invention, it is believed that inactivation of the membrane protein can be prevented even when a drug is encapsulated and used for DDS or the like. Therefore, its application to the field of nanomedicine is also expected.

As described above, the proteoliposome and biochip of the invention can be suitably used in a wide field of medicine, pharmaceuticals, diagnosis or the like from the viewpoint of excellent reliability.

EXAMPLES

Hereinafter, the present invention will be illustrated in detail with reference to examples and a comparative example. However, the invention is not limited by the following description.
Observation by AFM A mica substrate which is obtained in the present example was observed by an atomic force microscope (AFM, D3100, manufactured by Veeco) having an OMCL-TR800PSA-1 (manufactured by OLYMPUS CORPORATION) as a cantilever with the top of the mica substrate filled with a buffer solution B (30 mM HEPES, 260 mM KCl, 40 mM NaCl, and pH 7.4).

Production Example 1

Production of AMPA Receptor

An AMPA receptor was obtained by purifying High-Five cells (manufactured by Invitrogen Corporation) which were overexpressed, based on the method described in J. Biol. Chem., 279, 47975 (2004).

High-Five cells ($10^8$ cells) were homogenized by a Potter type homogenizer using a buffer solution for homogenization (containing a protease inhibitor, manufactured by Roche), and solubilized by an ultracentrifuge (manufactured by Beckman Coulter). Next, a solubilized fraction was purified with wheat germ agglutinins (WGA)-sepharose CL4B (Vector Laboratories), subsequently purified with diethylaminoethyl-sepharose CL6B (Amersham Bioscience), thereby obtaining 80 µg/ml of a purified AMPA receptor solution. The obtained AMPA receptor was confirmed by Western blotting using SDS-PAGE (electrophoresis) and silver staining, and an anti-GluR2/3 antibody derived from rabbit (manufactured by Chemicon) and an HRP-labeled anti-rabbit IgG antibody (Jackson Immuno Research Laboratories).

Example 1

With the use of, as lipid, mixed lipid (manufactured by Avanti Polar Lipids) of PC (egg yolk) and PS (derived from swine) in a ratio of 3:1; as membrane protein, AMPA receptors obtained in Production Example 1; and, as a surfactant, n-octyl-D-glucopyranoside (manufactured by Sigma), a mixed solution was obtained by mixing them with a buffer solution A (30 mM HEPES, 5 mM EDTA, 1 mM EGTA, 0.02% $NaN_3$ and pH 7.4) (room temperature, 10 minutes) such that the mixed lipid was 2.50 mM, the membrane protein was 125 nM, and the surfactant was 42 mM. The mixed solution was left to stand at room temperature for 10 minutes, dialyzed at 4° C. over 4 days, and then the surfactant was gradually removed to prepare a proteoliposome. A cellulosic membrane (molecular weight 14000, manufactured by Spectrum) was used for the semipermeable membrane. The buffer solution A was used as an external solution for dialysis.

Then, a solution containing the obtained proteoliposome 5 µl was added dropwise on a mica substrate (3 µm square), thereafter the mica substrate was washed twice with a buffer solution B, and a sufficient amount of the buffer solution B for observation was added on the mica substrate, followed by observation using AFM.

Examples 2 to 5

A proteoliposome was spread on a mica substrate in the same manner as in Example 1, except that the content of mixed lipid, membrane protein and surfactant were changed as shown in Table 1, and observation was made using AFM.

Comparative Example 1

A proteoliposome was spread on a mica substrate in the same manner as in Example 1, except that the content of mixed lipid, membrane protein and surfactant were changed as shown in Table 1, and observation was made using AFM.

TABLE 1

| | Lipid [mM] | Membrane Protein [nM] | Surfactant [mM] | $W_A + W_B$ (Calculated Value) [mM] |
|---|---|---|---|---|
| Example 1 | 2.50 | 125 | 42 | 20.0 |
| Example 2 | 2.30 | 145 | 38 | 18.4 |
| Example 3 | 2.20 | 145 | 42 | 17.6 |
| Example 4 | 2.80 | 104 | 46 | 22.4 |
| Example 5 | 3.00 | 83 | 50 | 24.0 |
| Comparative Example 1 | 3.70 | 85 | 31 | 29.6 |

Note that ($W_A + W_B$) (mM) in Table 1 is a calculated value of the maximum amount of the surfactant associating with lipid and membrane protein, in Examples and a Comparative Example.

Figure 2:
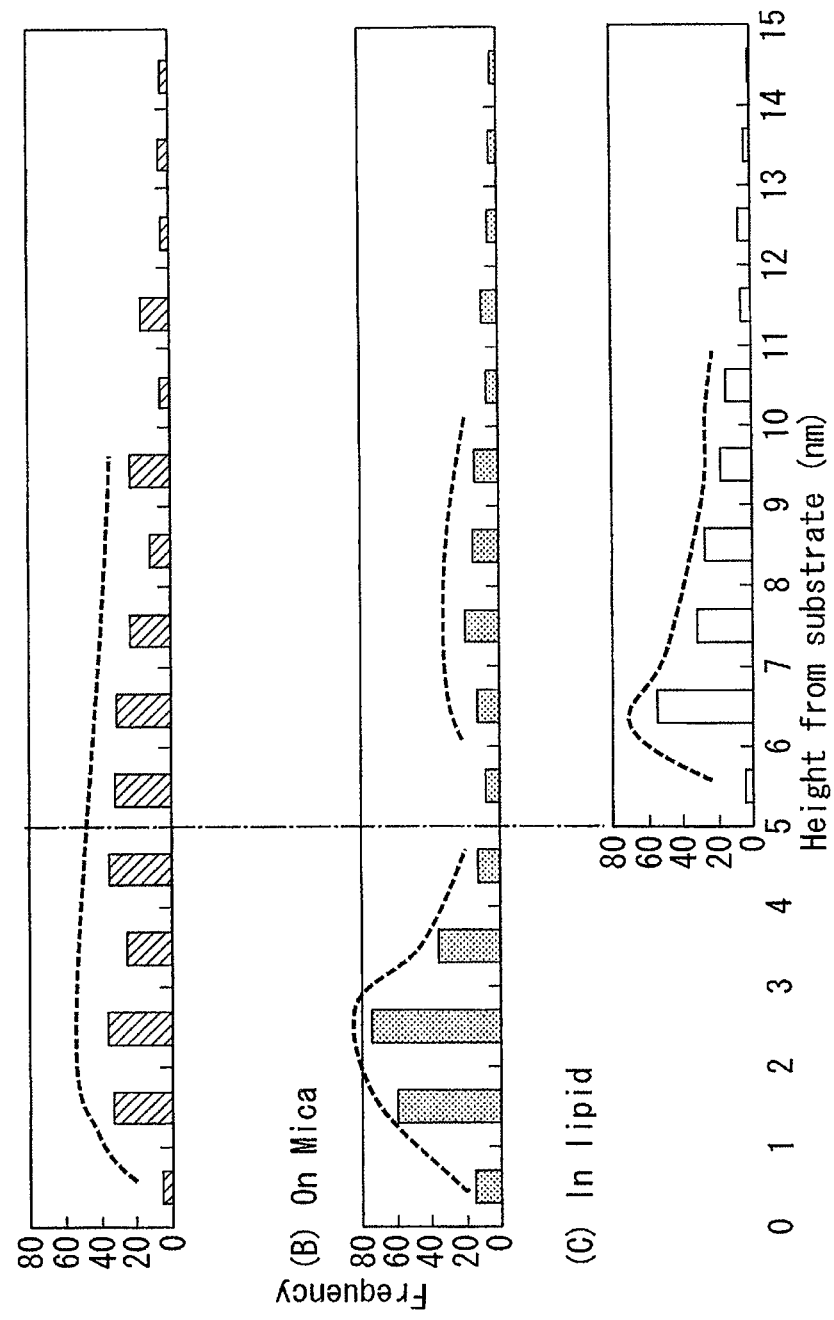
FIG. 2 shows a frequency distribution of height from a mica substrate of the membrane proteins of Example 1.

AFM images (3 μm in length×3 μm in width) obtained in Example 1 and Comparative Example 1 are shown in FIG. 1. In addition, the height (Y, nm) from the mica substrate on the white line of the AFM images (length X, nm) is also shown in FIG. 1. With regard to the membrane proteins on the mica substrate in Example 1, the frequency distribution of each height of those on the mica substrate, those located at the end of the lipid bilayer membrane and those located in the lipid bilayer membrane is shown in FIG. 2.

As shown in FIG. 1(A), in Example 1 in which a sufficient amount of the surfactant was used, a sufficiently large lipid bilayer membrane was formed on the mica substrate, aggregation of the membrane proteins was suppressed, and the proteins were dispersed at a predetermined interval with each other to reconstitute a lipid bilayer membrane. From the result shown in FIG. 2, it was confirmed that the membrane proteins which were located at the end of the lipid bilayer membrane were distributed widely from the height of the mica substrate to 2 to 9 nm, and some of them were aggregated. In contrast, it was confirmed that the height of the part outside the lipid bilayer membrane was approximately 2 to 3 nm, and aggregation was suppressed in the membrane proteins which were reconstituted in the lipid bilayer membrane.

The same results as in Example 1 were obtained in Examples 2 to 5 (not shown in FIGS.).

On the other hand, as shown in FIG. 1(B), in Comparative Example 1 in which the amount of the surfactant was small, the lipid domain which was formed on the mica substrate was very small, and the membrane proteins could not be reconstituted with sufficient dispersion in the lipid bilayer membrane.

In the proteoliposome and biochip according to embodiments of the invention, aggregation of membrane proteins which are reconstituted in a lipid membrane can be suppressed, and the membrane proteins can be spread at a predetermined interval for reconstitution. Accordingly, they can suitably be used in a wide range of fields such as medicine, pharmaceuticals, diagnosis or the like from the viewpoint of excellent reliability.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method for producing a proteoliposome by mixing lipid, membrane proteins and a surfactant to prepare a mixed solution, then removing the surfactant from the mixed solution,
   wherein the content of the surfactant in the mixed solution is made 2.0 times or more than the sum of a maximum amount of the surfactant associating with the lipid plus a maximum amount of the surfactant associating with the membrane protein,
   wherein a content of lipid in the mixed solution is 2.2 to 3.0 mM based on the total amount of the mixed solution,
   wherein a content of the membrane protein in the mixed solution is 83 to 145 nM based on the total amount of the mixed solution,
   wherein the lipid is at least one selected from the group consisting of phosphatidylcholine and phosphatidylserine,
   wherein the membrane protein is an ionotropic receptor, and
   wherein the surfactant is a nonionic surfactant.

2. The method of claim 1, further comprising spreading the proteoliposome on a substrate to produce a biochip.

3. The method according to claim 2, wherein the substrate includes at least one kind selected from the group consisting of mica, $SiO_2$, SiN, Au and Pt.

4. The method according to claim 1, wherein the membrane protein is an AMPA receptor.

5. The method according to claim 1, wherein the surfactant is a n-octyl-D-glucopyranoside.

\* \* \* \* \*